(12) United States Patent
Bentham et al.

(10) Patent No.: US 6,680,334 B2
(45) Date of Patent: Jan. 20, 2004

(54) CRYSTALLINE MATERIAL

(75) Inventors: Alan Craig Bentham, Sandwich (GB); Alan John Pettman, Sandwich (GB); Keith Stephen Ruddock, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/224,663

(22) Filed: Aug. 20, 2002

(65) Prior Publication Data

US 2003/0119883 A1 Jun. 26, 2003

Related U.S. Application Data

(60) Provisional application No. 60/327,155, filed on Oct. 3, 2001.

(30) Foreign Application Priority Data

Aug. 28, 2001 (GB) .............................................. 0120808

(51) Int. Cl.⁷ ........................ C07D 207/40; A61K 31/44
(52) U.S. Cl. ........................................ 514/355; 546/321
(58) Field of Search ............................ 514/355; 546/321

(56) References Cited

U.S. PATENT DOCUMENTS 6,057,344 A    5/2000    Young ........................ 514/356

FOREIGN PATENT DOCUMENTS

| EP | 0089167 | 10/1986 | ......... C07D/211/90 |
| EP | 0244944 | 1/1990 | ......... C07D/211/90 |
| EP | 0566142 | 10/1993 | ......... A61K/47/48 |
| EP | 0599220 | 8/1996 | ......... C07D/211/90 |
| EP | 1013275 | 6/2000 | ......... A61K/31/44 |
| EP | 0902016 | 5/2002 | ......... C07D/211/90 |
| WO | 9925688 | 5/1999 | ......... C07D/211/90 |
| WO | 9925689 | 5/1999 | ......... C07D/211/90 |
| WO | 9952873 | 10/1999 | ......... C07D/211/90 |
| WO | 0024714 | 5/2000 | ......... C07D/209/48 |
| WO | WO 00/73271 A1 * | 12/2000 | ......... C07D/207/40 |
| WO | 0102360 | 1/2001 | ......... C07D/211/90 |

OTHER PUBLICATIONS

Arrowsmith, J. E., et al., *J. Med. Chem.*, 29, pp. 1696–1702 (1986).
Arrowsmith, J. E., et al., *J Med. Chem.*, 32, pp. 562–568 (1989).
Alker, D., et al., *J. Med. Chem.*, 33, pp. 585–591 (1990).
Alker, D., et al., *J. Med. Chem.*, 33, pp. 1805–1811 (1990).
Alker, D., et al., *J. Med. Chem.*, 34, pp. 19–24 (1991).
Atwal, K. S., et al., *J. Med. Chem.*, 34, pp. 806–811 (1991).
Rovnyak, G. C., et al., *J. Med. Chem.*, 35, pp. 3254–3263 (1992).
Richter Gedeon Vegyeszeti Gyar, *HU 217345–B* (1994).
Richter Gedeon Vegyeszeti Gyar, *HU 217346–B* (1994).
Boryung Pharm Co. Ltd., *KR 98031367–A* (1996).
*Dihydropyridines in Action*, Hobsons Press (1989).

\* cited by examiner

Primary Examiner—Zinna Northington Davis
(74) Attorney, Agent, or Firm—Garth Butterfield; Peter C. Richardson

(57) ABSTRACT

The present invention relates to amlodipine free base in a crystalline form, to pharmaceutical formulations comprising such material, processes of manufacture and its use in therapy.

10 Claims, 1 Drawing Sheet

CRYSTALLINE MATERIAL

This is a non-provisional application claiming priority from provisional application, Serial No. 60/327,155, filed Oct. 3, 2001.

Priority is hereby claimed of previously filed foreign application, GB 0120808.1, filed Aug. 28, 2001 (37 C.F.R. §1.55(a)), which was filed under the Paris Convention for the Protection of Industrial Property and was filed in the United Kingdom with, and received by The Patent Office, Cardiff Road, Newport, South Wales, NP10 8QQ.

This invention relates to a new crystalline, pharmaceutically acceptable, form of amlodipine free base, processes for its synthesis and its use in pharmaceutical compositions.

Amlodipine, 2-[(2-aminoethoxy)]-methyl-4-(2-chlorophenyl)-3-ethoxycarbonyl-5-methoxycarbonyl-6-methyl-1,4-dihydropyridine, is a calcium channel blocking agent with a long duration of action which has been approved world-wide, as its benzenesulfonate (besylate) salt, for use in the treatment of ischaemic heart disease and hypertension. The compound exists as (+/−) isomers, with most of the activity residing in the (−) isomer, which can be isolated by standard techniques, if so desired.

A number of European (EP) and International (WO) patent applications relate to amlodipine and its salts. Amlodipine and salts thereof were first disclosed by the present applicants in EP89167. The besylate salt of amlodipine was first disclosed in EP244944. WO01/02360, EP0902016, EP566142, EP599220 and Hungarian Patent Application No. 217346 describe processes for the preparation of salts of amlodipine. The free base formed is not isolated. WO99/52873 describes various organic and non-organic salts of amlodipine, but is silent on the free base. WO00/24714 describes processes for the preparation of the phthalimide derivatives of amlodipine, but is silent as to preparation or isolation of the free base. WO99/25688 describes the preparation of amlodipine free base prior to salt formation. However, no details are provided as to the physical form of the material, which is in a crude form from work-up of the reaction mixture and therefore, it is submitted, is likely to be in the form of an oil. U.S. Pat. No. 6,057,344 and EP1013275 describe methods of treatment comprising (−) amlodipine and its salts, although no preparation or isolation of the free base is described. WO99/11259 describes compositions comprising a combination of amlodipine and atorvastatin and is silent on any preparation of amlodipine free base.

In the non-patent literature, preparation of amlodipine, as its maleate salt, was first described in J. Med. Chem 1986, 29, 1696. A reaction scheme describing the production synthesis of amlodipine besylate via the free base is described in an undergraduate resource material entitled 'Dihydropyridines In Action', Hobsons Publishing, 1989 (ISBN:/85324 280 2). No explicit reaction conditions are described to accompany the scheme.

It is submitted that none of the listed prior art explicitly discloses the preparation and characterisation of amlodipine free base in a solid form. The prior art comprises numerous disclosures of salt formations of amlodipine, which teaches away from the utility of amlodipine free base itself as a pharmaceutical product. In fact, solid free base initially synthesised by the present applicants 'in-house' was characterised as a poorly soluble and low-melting point material, which was unsuitable for formulation. Furthermore, amlodipine is known to undergo an internal reaction to afford a cyclic impurity rendering it unsuitable for formulation and it was hypothesised that solid amlodipine free base would undergo such a reaction. See scheme 1.

Scheme 1

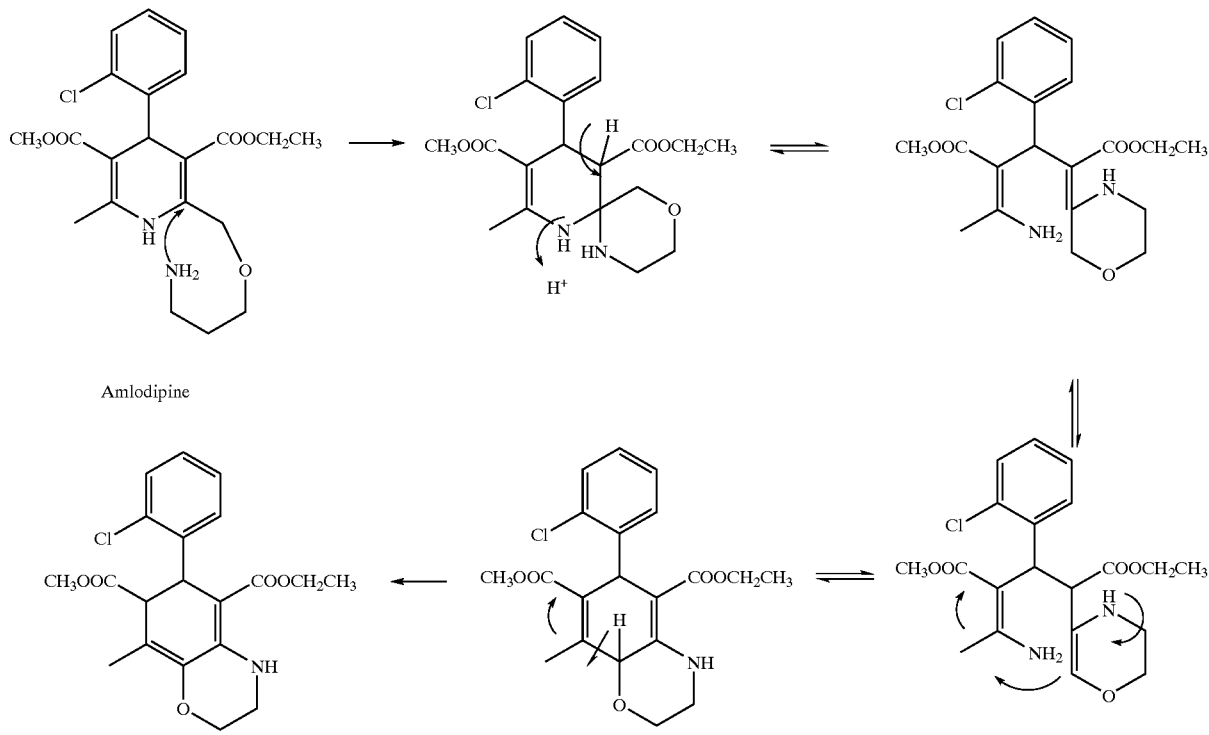

When amlodipine is treated to form an addition salt with a strong acid, the propensity for the internal reaction is reduced due to protonation of the free amino group. Hence, the teaching of the prior art is to form addition salts with sufficiently strong acids such as benzene sulfonic acid or maleic acid and the result is a prejudice in the art away from the utility of free base material.

Surprisingly, the present inventors have found that amlodipine free base in a crystalline form can be prepared and has a melting point and, most surprisingly, a solubility profile which renders it suitable for pharmaceutical formulation. Such a solubility profile was unexpected, based on the 'in-house' knowledge of the properties of initially synthesised free base material. Furthermore, the crystalline material has sufficient stability for long term storage and use and does not undergo the internal reaction described above to any significant extent.

Thus, as a first aspect, the present invention provides a crystalline form of amlodipine free base. As a preferred aspect, the crystalline material is free from amorphous free base material.

Crystalline amlodipine free base according to the present invention has all the characteristics of a normal crystal structure, i.e. it forms a regular crystal lattice. It will be clear to the skilled person that materials which exist in a crystalline state may exist in a number of different polymorphic forms. Polymorphs may be identified by well-known techniques and all polymorphs of crystalline amlodipine free base are envisioned by the present invention. Crystals of amlodipine free base may be characterised in terms of their x-ray diffraction (XRD) pattern, which produces a read-out based on the lattice structure of the crystal. It is well known to those skilled in the art that different polymorphic forms of a material may be distinguished in terms of the XRD patterns.

BRIEF DESCRIPTION OF DRAWING

Thus.

Figure 1:
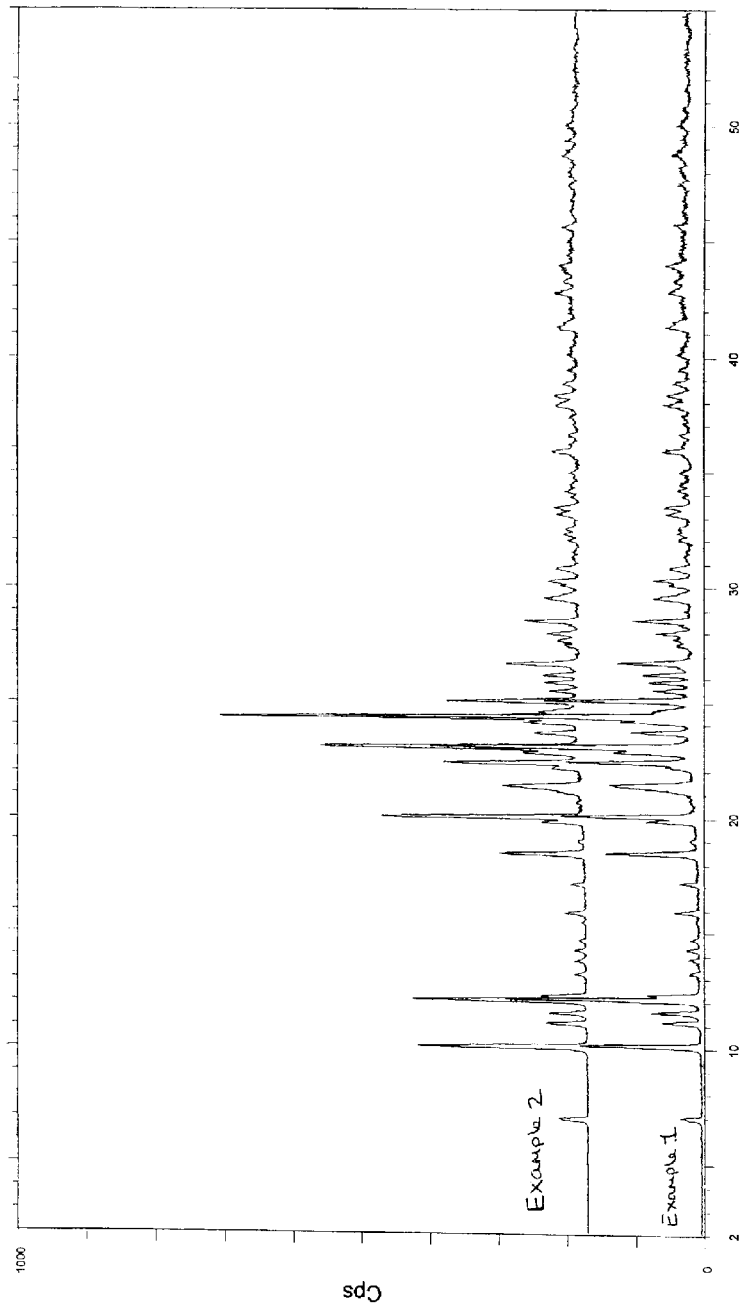
FIG. 1 presents an XRD pattern of a crystalline form of amlodipine free base. Data was obtained using the following technique. The material was mounted on a silicon wafer and rotated to reduce the effects of particle size and orientation. The sample was exposed to X-ray radiation using $CuK_{\alpha 1}(\lambda=1.5406 \text{ Å})$ and scanned through an angular range of 2° to 55° 2θ on a Siemens D5000 powder X-Ray diffractometer equipped with variable slits and a graphite secondary monochromator. Results may be tabulated as percentage intensities for an angular range of 2–55°.

Crystalline amlodipine free base may be used in the treatment of disease. Use of crystalline amlodipine free base as a therapeutic agent, compared to a salt form, has the advantage of obviating a final salt formation step, thereby providing cost and time savings. Thus, as a further aspect of the present invention, there is provided the use of crystalline amlodipine free base in human or veterinary therapy, particularly human, most particularly in the treatment of ischaemic heart disease and hypertension.

As a further aspect, the present invention provides the use of crystalline amlodipine free base in the manufacture of a medicament for the treatment of ischaemic heart disease or hypertension.

Alternatively, the present invention provides a method of treating a patient, particularly a human patient, suffering from ischaemic heart disease or hypertension, comprising administration of an effective amount of crystalline amlodipine free base.

Furthermore, crystalline amlodipine free base may be combined with a pharmaceutical diluent and/or carrier to provide pharmaceutical compositions suitable for use in therapy. A formulation comprising crystalline amlodipine free base has a reduced effective mass of active material compared to a corresponding salt formulation. Therefore, since less material is required to be incorporated into formulations such as tablets, tablet size may be reduced, resulting in improved patient convenience and the likelihood of increased patient compliance.

Crystalline amlodipine free base may be formulated for oral, buccal, parenteral, transdermal, topical (including ophthalmic and nasal), depot or rectal administration or in a form suitable for administration by inhalation or insufflation (either through the mouth or nose). Particularly suitable means for administration of crystalline amlodipine free base are equivalent to those for amlodipine besylate and related salt forms as set out in EP0244944 in Examples 2, 3 and 4, which are incorporated herein by reference, such as tablet, capsule and sterile aqueous compositions.

Crystalline amlodipine free base can be administered alone but will generally be administered in admixture with a suitable pharmaceutical excipient, diluent or carrier selected with regard to the intended route of administration and standard pharmaceutical practice.

For example, crystalline amlodipine free base can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The crystalline amlodipine free base may also be administered as fast-dispersing or fast-dissolving dosage forms or in the form of a high energy dispersion or as coated particles. Suitable formulations of crystalline amlodipine free base may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

The tablets may be manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, crystalline amlodipine free base may be combined with various sweetening or flavouring agents, colouring matter or dyes, with emulsifying and/or suspending agents and with diluents such as water, ethanol, propylene glycol and glycerin, and combinations thereof.

Crystalline amlodipine free base can also be formulated for administration parenterally, for example, intravenously, intra-arterially, intraperitoneally, intrathecally, intraventricularly, intraurethrally, intrasternally, intracranially, intramuscularly or subcutaneously, or it may be administered by infusion or needleless injection techniques. For such parenteral administration it is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Crystalline amlodipine free base can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insulator may be formulated to contain a powder mix of crystalline amlodipine free base and a suitable powder base such as lactose or starch.

Alternatively, crystalline amlodipine free base can be administered in the form of a suppository or pessary, or it may be applied topically in the form of a gel, hydrogel, lotion, solution, cream, ointment or dusting powder. Crystalline amlodipine free base may also be dermally or transdermally administered, for example, by the use of a skin patch. It may also be administered by the pulmonary or rectal routes.

Crystalline amlodipine free base may also be administered by the ocular route, particularly for treating diseases of the eye. For ophthalmic use, the compound can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, it may be formulated in an ointment such as petrolatum.

For application topically to the skin, crystalline amlodipine free base can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyidodecanol, benzyl alcohol and water.

Crystalline amlodipine free base may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

As a further aspect of the present invention, crystalline amlodipine free base may be combined with other physiologically active agents and formulated for suitable administration. Suitable further pharmaceutically active agents include atorvastatin, according to WO99/11259 or ACE inhibitors, such as those licensed for use in treating hypertension, such as benazepril, benazeprilat, captopril, enalapril, enalaprilat, fosinopril sodium, lisinopril, pentopril, perindopril, quinapril hydrochloride, quinaprilat, ramipril, ramiprilat, trandolapril, zofenopril calcium, and the like.

Compositions comprising crystalline amlodipine free base may contain from 0.1% upwards, e.g. 0.1–99% of the active material, depending on the method of administration. A proposed dose of crystalline amlodipine free base of the invention is between 2–15 mg/patient per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Although the direct use of crystalline amlodipine free base in therapy is envisaged, the superior handling and storage qualities of the material render it suitable for use in the preparation of a salt or solvate form. Suitable pharmaceutically acceptable salts include acid addition salts such as the hydrochloride, hydrobromide, hydroiodide, bisulphate, acid citrate, bitartrate, ethansulphonate, sulphate, phosphate or acid phosphate, acetate, maleate, fumarate, lactate, tartrate, citrate, gluconate, benzenesulphonate (besylate), p-toluenesulphonate (tosylate), methanesulphonate (mesylate), succinate, salicylate and nitrate. The besylate salt is preferred. Thus, as a yet further aspect, the present invention provides the use of crystalline amlodipine free base in the manufacture of a salt, preferably the besylate, or solvate of amlodipine. Furthermore, the invention provides a process for the preparation of a salt of amlodipine comprising treatment of crystalline amlodipine free base with a suitable acid, such as benzene sulfonic acid, in a suitable solvent.

The present invention extends to processes by which crystalline forms of amlodipine free base may be prepared. As a preferred aspect, there is provided a process for the preparation of crystalline amlodipine free base comprising treatment of a corresponding salt form under suitable aqueous basic conditions. For example, the free base may be isolated from the salt by treatment with aqueous base, e.g. sodium hydroxide, partitioning the organic and aqueous layers with a suitable organic solvent, separating, drying and evaporating the organic solution under vacuum. Further, there is provided a process for the preparation of crystalline amlodipine free base comprising crystallisation of non-crystalline amlodipine free base in a suitable solvent or mixture of solvents. Suitably, crystalline amlodipine free base may be crystallised from isopropyl alcohol or toluene.

The present invention is illustrated by the following non-limiting examples.

EXAMPLE 1

Isolation of Amorphous Amlodipine Free Base

Amlodipine besylate (30 g) was slurried into a mixture of dichloromethane/water (1:1, 500 ml) and the rapidly slurred emulsion was basified to pH 11 with aqueous sodium hydroxide (5M). The resulting organic layer was separated and the remaining aqueous layer extracted with dichloromethane (100 ml). The combined extracts were washed with water (150 ml) dried (MgSO$_4$) and evaporated in vacuo to afford an off-white solid (20.3 g).

Melting point: 140–140.7° C.

$^1$H NMR (CDCl$_3$) δ 1.18 (3H, t),1.30 (2H, s), 2.34 (3H, s), 2.93 (2H, m), 3.56 (5H, m), 4.05 (2H, q), 4.72 (2H, q), 5.40 (1H, s), 7.03 (1H, t), 7.11 (1H, t), 7.23 (1H, d), 7.38 (1H, d), 7.80 (1H, s).

EXAMPLE 2

Crystallisation of Amlodipine Free Base from Toluene

Amorphous amlodipine free base (10 g) was slurried in toluene (2 ml/g) overnight. The resulting solid was isolated by filtration and dried in vacuo at 45° C. to give a white solid (7.53 g).

DSC melting point: 145.04° C.

Powder X-ray Diffraction Pattern—see FIG. 1 and Table 1, below.

TABLE 1

| Angle | Intensity % |
|---|---|
| 6.8 | 8.3 |
| 9.9 | 46.4 |
| 11.0 | 11.7 |
| 11.4 | 10.9 |
| 12.0 | 47.7 |
| 12.1 | 13.7 |
| 13.1 | 3.8 |
| 13.7 | 3.8 |
| 14.1 | 3.8 |
| 14.6 | 2.9 |
| 15.4 | 2.2 |
| 15.8 | 6.5 |
| 17.0 | 5 |
| 18.4 | 24.1 |
| 18.9 | 2.9 |
| 19.7 | 12.4 |
| 20.0 | 56.2 |
| 20.6 | 3.3 |
| 21.2 | 23.4 |
| 22.1 | 10.1 |
| 22.3 | 39.3 |
| 22.7 | 17.4 |
| 23.0 | 73.1 |
| 23.6 | 14.9 |
| 24.0 | 15.7 |
| 24.3 | 100 |
| 24.6 | 14.2 |
| 25.0 | 38.2 |
| 25.4 | 10.8 |
| 25.7 | 12.3 |
| 26.1 | 12.5 |
| 26.6 | 22.3 |
| 27.4 | 5.9 |
| 27.6 | 8.4 |
| 27.9 | 11.4 |
| 28.5 | 17.3 |
| 29.5 | 12 |
| 30.0 | 7.7 |
| 30.2 | 11 |
| 30.8 | 8.9 |
| 31.2 | 4.6 |
| 31.5 | 4.7 |
| 31.9 | 5.7 |
| 32.2 | 6.8 |
| 32.5 | 6.3 |
| 33.1 | 8.6 |

TABLE 1-continued

| Angle | Intensity % |
|---|---|
| 33.4 | 9.4 |
| 33.8 | 5 |
| 34.1 | 6.2 |
| 34.4 | 5.3 |
| 34.9 | 4.9 |
| 35.8 | 10 |
| 36.1 | 5.8 |
| 36.6 | 5.3 |
| 37.4 | 5.3 |
| 37.9 | 9.1 |
| 38.3 | 9.2 |
| 38.8 | 7.1 |
| 39.4 | 5.9 |
| 40.1 | 6.1 |
| 40.4 | 5.2 |
| 41.2 | 7.9 |
| 42.8 | 9.4 |
| 43.3 | 6.8 |
| 43.7 | 6.9 |
| 43.9 | 8.2 |
| 45.6 | 7.5 |
| 46.3 | 5.5 |
| 47.4 | 5.7 |
| 47.9 | 5.4 |
| 48.7 | 7.7 |
| 49.4 | 5.9 |
| 50.1 | 6.5 |
| 50.7 | 5.5 |
| 51.5 | 4.3 |
| 53.4 | 4.4 |

Solubility
SGN pH: 1.20 >5.00 mg/ml
Acetate pH: 5.93 >5.00 mg/ml
Phosphate pH: 7.71 0.72 mg/ml
Glycine pH: 9.25 0.13 mg/ml
NaOH pH: 11.44 <0.05 mg/ml

EXAMPLE 3

Crystallisation of Amlodipine Free Base from Isopropyl Alcohol

Crystallisation was repeated with isopropyl alcohol under identical conditions to those outlined in Example 2 to afford a white solid (8.20 g).

DSC melting point: 143.57° C.

Tablet Formulation

Amlodipine free base (1.00 g), was blended into a tablet formulation using a suitable mixture of excipients (Avicel microcrystalline cellulose, dicalcium phosphate, a disintegrant and a lubricant) to a total weight of 100 g. The formulation was mixed and screened and the blend compressed into tablets using a compaction simulator with a range of applied forces. The formulation produced tablets of good crushing strength ranging from 18–25 Kp.

| Material | g/100 g |
|---|---|
| Amlodipine Free Base | 1.00 |
| Avicel PH102 | 64.00 |
| Dibasic Calcium Phosphate | 32.00 |
| ExploTab CLV | 2.00 |
| Magnesium Stearate | 1.00 |

Stability Data

The stability of crystalline amlodipine free base bulk and amlodipine free base tablets was assessed by storing samples for up to 6 or 12 weeks at 25° C./60% RH, 40° C./75% RH and 50° C./20% RH. Changes were monitored using a stability-indicating HPLC method. Results were calculated by normalised peak area (npa). Degradants were identified by comparison of their relative retention times against impurity standards.

The only known degradant formed in amlodipine free base bulk and tablets was Compound 1 (see below).

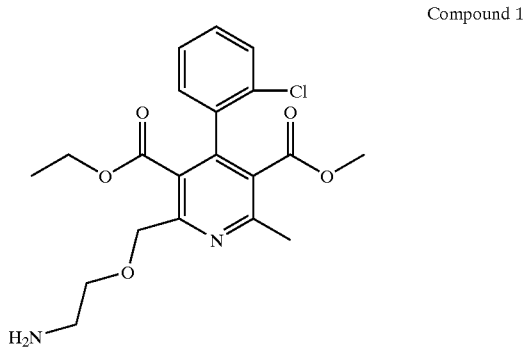

Compound 1

(i) Amlodipine Free Base Bulk

It was found that crystalline amlodipine free base is stable with respect to formation of known and unknown degradants for up to 12 weeks when stored under normal conditions of temperature and humidity. Similarly, stability was demonstrated at elevated temperatures and humidity.

(ii) Amlodipine Free Base Tablets

Crystalline amlodipine free base tablets stored at 25° C./60%RH for up to 6 weeks are stable with respect to the formation of known and unknown degradants.

What is claimed is:

1. A crystalline form of the free base of 2-[(2-aminoethoxy)]-methyl-4-(2-chlorophenyl)-3-ethoxycarbonyl-5-methoxycarbonyl-6-methyl-1,4-dihydropyridine (amlodipine).

2. A method of treating ischaemic heart disease or hypertension in a human patient comprising administration of an effective amount of crystalline amlodipine free base.

3. A pharmaceutical composition comprising crystalline amlodipine free base and one or more pharmaceutically acceptable diluents or carriers and, optionally, one or more other physiologically active agents.

4. A process for the preparation of crystalline amlodipine free base comprising the steps of:

(i) isolating amlodipine free base; and (ii) crystallising the material obtained in (i) using a suitable solvent or mixture of solvents.

5. A process according to claim 4 wherein said step (i) comprises:

(a) contacting a salt form of amlodipine with an aqueous base;

(b) partitioning an organic layer and an aqueous layer by contact with an organic solvent; and (c) separating and recovering said organic layer.

6. A process according to claim 5 wherein said salt form of amlodipine is amlodipine besylate; said aqueous base is aqueous sodium hydroxide; and said organic solvent is dichloromethane.

7. A process according to claim 4 wherein said step (ii) comprises steps of:

(a) contacting said amlodipine free base in at least one crystallizing solvent; and (b) recovering crystallized amlodipine free base.

8. A process according to claim 7 wherein said crystallizing solvent is isopropyl alcohol or toluene.

9. A pharmaceutical salt or solvate comprising a pharmaceutically acceptable acid addition salt of the crystalline form of the free base of claim 1.

10. A pharmaceutical salt or solvate according to claim 9 wherein the pharmaceutical acceptable acid addition salt is besylate salt.

* * * * *